United States Patent [19]

Clifford et al.

[11] Patent Number: 5,206,158
[45] Date of Patent: Apr. 27, 1993

[54] PROCESS FOR THE PREPARATION OF DIFLUOROBENZAMIDE

[75] Inventors: Kenneth H. Clifford, Sittingbourne; Philip J. Geary, Ashford; Robert J. Pryce, Faversham, all of United Kingdom

[73] Assignees: Gist-Brocades N.V., Delft; Shell Internationale Research Maatschappij B.V., The Hague, both of Netherlands

[21] Appl. No.: 569,729

[22] Filed: Aug. 21, 1990

Related U.S. Application Data

[63] Continuation of Ser. No. 60,552, Jun. 11, 1987, abandoned.

[30] Foreign Application Priority Data

Jul. 2, 1986 [GB] United Kingdom ............... 8616160

[51] Int. Cl.$^5$ ...................... C12P 13/02; C12N 1/20
[52] U.S. Cl. ................... 435/129; 435/253.2; 435/252.1; 435/872
[58] Field of Search ............ 435/129, 872, 863, 253.1, 435/253.2, 252.1

[56] References Cited

U.S. PATENT DOCUMENTS 4,629,700  12/1986  Prevatt ................................ 435/128

FOREIGN PATENT DOCUMENTS 0133927  3/1985  European Pat. Off. ............ 435/129

OTHER PUBLICATIONS

Goodfellow et al., *The Biology of the Actinomycetes*, Academic Press, 1984, pp. 91–94.
Harper, D, *Biochem J.* vol. 165, pp. 309–319, 1977.

*Primary Examiner*—Irene Marx

[57] ABSTRACT

The invention provides a process for the preparation of 2,6-difluorobenzamide which comprises subjecting 2,6-difluorobenzonitrile to the action of a suitable hydrolysing microorganism or nitrilase extract therefrom; and Rhodococcus Sp. NCIB 12218 or a mutant thereof, suitable for use in the process.

2 Claims, No Drawings

PROCESS FOR THE PREPARATION OF DIFLUOROBENZAMIDE

This application is a continuation of application Ser. No. 07/060,552, filed Jun. 11, 1987, now abandoned.

This invention relates to a process for the preparation of 2,6-difluorobenzamide.

EP-A-133 927 (nitto) discloses the conversion of a nitrile compound to the corresponding amide by the action of certain suitable microorganisms. These microorganisms are generally improved in their activity by irradiation with light. Specific types of microorganism disclosed as suitable are gram-positive bacteria of the genera:
(a) Cornyebacterium;
(b) Nocardia;
(c) Bacillus;
(d) Bacteridium;
(e) Micrococcus; and
(f) Brevibacterium.

The prime utility disclosed is production of acrylamide from acrylonitrile and nicotinic acid from cyanopyridine. Additional conversions specifically disclosed are conversions of acetonitrile to acetamide, methacrylonitrile to methacrylamide, valeronitrile to valeramide, benzonitrile to benzamide, propionitrile to propionamide, n-butyronitrile to n-butyramide, malonitrile to malonamide, succinonitrile to succinamide, fumaronitrile to fumaramide, chloroacetonitrile to chloroacetamide and β-hydroxypropionitrile to β-hydroxypropionamide.

D.B. Harper, "Microbial Metabolism of Aromatic Nitriles", Biochem. J. (1977) 165, 309–319 describes the metabolism of benzonitrile (to benzoic acid) by Nocardia Sp. (rhodochrous group) NCIB 11216 and the isolation and properties of its nitrilase enzyme. Table 4 on Page 317 discloses the relative rates of hydrolysis by the enzyme of various substituted benzonitriles. It appears that the rate is very much affected by steric hindrance afforded by a substituent in the 2-position. Thus the rate for 2-fluorobenzonitrile is less than 30% of that for benzonitrile, and the rates for 2-chlorobenzonitrile and 2-methylbenzonitrile are substantially zero, whereas the rates for 4-fluorobenzonitrile, 4-chlorobenzonitrile and 4-methylbenzonitrile are significantly greater than that for benzonitrile. It may reasonably be predicted therefore that a 2,6-disubstituted benzonitrile, being even more sterically hindered, would be wholly unsusceptible to the enzymatic hydrolysis. Indeed, Harper found that 2,6-dichlorobenzonitrile (the herbicide Dichlobenil) was not attacked even at high concentrations. Even 3,5-dibromobenzonitrile (the herbicide Bromoxynil) remained unattacked at high concentrations of the enzyme, notwithstanding the fact that the rate of hydrolysis for 3-bromobenzonitrile was more than 70% greater than for benzonitrile. Harper also records that Verloop, Residue Rev. 43 (1972) 55–103 found that mono-orthosubstitution decreases rate of alkaline hydrolysis of aromatic nitriles but di-ortho substitution completely inhibits the process.

It has now surprisingly been discovered that 2,6-difluorobenzonitrile can be hydrolysed microbially. Furthermore, a novel microorganism has surprisingly been found which is capable of hydrolysing 2,6-difluorobenzonitrile at a faster rate than benzonitrile per se.

According to the present invention therefore there is provided a process for the preparation of 2,6-difluorobenzamide which comprises subjecting 2,6-difluorobenzonitrile to the action of a suitable hydrolysing microorganism or nitrilase extract therefrom.

Suitable hydrolysing microorganisms may be gram positive bacteria having nitrilase activity of the genera Corynebacterium, Nocardia, Bacillus, Bacteridium, Micrococcus and Brevibacterium. However, the microorganism is preferably a bacterium of the genus Rhodococcus. Conveniently the microorganism per se is used in the process, but if desired nitrilase extract obtained from the microorganism in known manner may be used instead.

A preferred example of a species of bacterium of the genus Rhodococcus has been obtained as a soil isolate from the sludge treatment plant at Shell Haven Refinery, Stanford-le-Hope, Essex. England and has been deposited at the National Collection of Industrial Bacteria (NCIB), Torrey Research Station, 135 Abbey Road, Aberdeen AB9 8DG, Scotland, on 13th Mar. 1986 under the provisions of the Budapest Treaty on the International Recognition of the Deposit of Microorganisms for the Purposes of Patent Procedure and has been assigned accession number NCIB 12218. This microorganism is herein referred to as "Rhodococcus Sp. NCIB 12218".

This novel microorganism, Rhodococcus Sp. NCIB 12218, is, as will be described in detail hereinafter, capable of hydrolysing 2,6-diflurobenzonitrile at a faster rate than it hydrolyses benzonitrile per se.

Accordingly in the process of the invention the microorganism is preferably Rhodococcus Sp. NCIB 12218 or a mutant thereof and is conveniently Rhodococcus Sp. NCIB 12218.

The invention also comprises Rhodococcus Sp. NCIB 12218 and mutants thereof.

Mutants of Rhodococcus Sp. NCIB 12218 may be generated, isolated and selected by known procedures. Thus mutation may be by chemical means, e.g. using N-methyl-N'-nitro-N-nitro-soguanidine, or by physical means employing ultraviolet radiation.

The invention also extends to 2,6-difluorobenzamide whenever prepared by the process of the invention and to the use of 2,6-difluorobenzamide whenever so prepared in the preparation of an insecticidal compound. 2,6-Difluorobenzamide is a known intermediate for the preparation of known insecticidal compounds, e.g. diflubenzuron (see UK Patent Specification No. 1,324,293). Other processes using 2,6-difluorobenzamide as an intermediate for insecticidally active compounds include those described in UK Patent Specification No. 1,460,419 and EP-A-161 019.

Microorganisms for use in the process of the invention may be grown on a suitable known growth medium containing an assimilable carbon source (e.g. glucose, lactose or sucrose), an assimilable nitrogen source (e.g. ammonium sulphate, ammonium nitrate or ammonium chloride), a source of organic trace nutrients (e.g. yeast extract, malt extract, peptone, or meat extract) and inorganic trace nutrients (e.g. phosphate, magnesium, potassium, calcium, manganese, zinc and/or iron salts). Growth is generally effected at a temperature in the range 20 to 37° C. and a pH in the range 5 to 9, with agitation (e.g. by shaking or stirring) in the presence of oxygen or air. Cells may be harvested in known manner and if desired kept on agar slopes, frozen or lyophilised before use in the process of the invention.

The process of the invention may conveniently be effected at a temperature in the range 0 to 37° C., preferably 20 to 30° C, at a pH in the range 6 to 9, preferably 7 to 8, and preferably with irradiation by light.

Rhodococcus Sp. NCIB 12218 has been characterised and identified by the NCIB as follows: Tests were at 30° C. and growth was on Oxoid CM3 Nutrient Agar unless otherwise stated.

Cell Morphology

After growth for 5 hours at 30° C. on Oxoid CM1 Nutrient broth +0.75%w agar, by phase contrast at ×630 magnification cells are small parallel-.sided slightly bent or curved rods, with some clustering of cells.

Gram positive

Spores -

Motility 0

Colonial Morphology

After 3 days growth, colonies are round, regular, entire, smooth, opaque, low convex, very pale pink and approximately 1 mm in diameter.

Growth on Glucose Peptone Water Sugars

37° C.±trace
45° C.—

Catalase+

Oxidase, Kovacs

O-F glucose Oxidative

"O-F glucose" was performed using the oxidation-fermentation medium of Hayward and Hodgkiss, J.Gen. Microbiol. 26 (1961) 133–140, supplemented with 1%w filter-sterilised D-glucose. A tube sample was inoculated with Rhodococcus Sp. NCIB 12218 and incubated for 14 days.

Rhodococcus Sp. NCIB 12218 can conveniently be stored on nutrient agar slopes at 4° C., or cells may be isolated in buffer medium and stored at low temperatures, e.g. −15° C. It has been found possible to store cells at −15° C. for a month without loss of activity.

The invention will be further understood from the following Examples.

EXAMPLE 1

Growth medium was made up from the following constituents:
2.0 g $K_2HPO_4$
0.2 g $MgSO_4.7H_2O$
2.5 mg $FeSO_4.7H_2O$
12.5 mg $CaCl_2.2H_2O$
2.5 mg $MnSO_4.3H_2O$
1.0 g $(NH_4)_2SO_4$
10 g Glucose
5 g Peptone
3 g Yeast extract
3 g Malt extract These constituents were dissolved in 900 ml water, pH was adjusted to 7.2 by addition of hydrochloric acid and the solution was made up to 1 litre by addition of water.

50 ml of the above growth medium in a 250 ml conical flask was inoculated with Rhodococcus Sp. NCIB 12218 and incubated at 30° C. on a shaker for 48 hours.

Cells were harvested by centrifugation (at 20,000 rpm for 15 minutes on a "Sorvall" (trade mark) centrifuge), were washed with a 50mM phosphate buffer of pH 8, recentrifuged and were resuspended in 2.5 ml of the buffer. A small sample of the suspension was removed and used to determine the dry weight of the cells therein.

A quantity of the suspension calculated to contain 0.5mg dry weight of Rhodococcus Sp. NCIB 12218 cells was diluted to 1 ml with the above buffer. The suspension was maintained at 25° C. and was irradiated for 5 minutes by means of a 60 W tungsten lamp at a distance of 25 cm before addition of 1 mg of 2,6-difluorobenzonitrile (DFBN). Irradiation was continued and the mixture was maintained at 25° C. for 15 minutes after the addition of DFBN. A sample was then withdrawn and analysed by gas chromatography (gc) for DFBN and 2,6-difluorobenzamide (DFBAM) to determine the extent of reaction.

The above procedure was repeated for comparative purposes using benzonitrile and 2,6.dichlorobenzonitrile in place of the DFBN. Results are given in Table I following.

TABLE 1

| Substrate | Product | Productivity |
|---|---|---|
| 2,6-difluoro-benzonitrile | 2,6-difluorobenz-amide | 25.5 g/g cells/hour (0.178 mol/g cells/hour) |
| benzonitrile | benzamide | 15.6 g/g cells/hour (0.146 mol/g cells/hour) |
| 2,6-dichloro-benzonitrile | 2,6-dichlorobenz-amide | 0.053 g/g cells/hour ($3 \times 10^{-4}$ mol/g cells/hour) |

EXAMPLE 2

400 ml of the growth medium of Example 1 was inoculated with Rhodococcus Sp. NCIB 12218 and incubated at 30° C. for 48 hours.

The resulting cells were harvested and washed as in Example 1 and were suspended (440 mg dry weight) in 2 liters of the phosphate buffer of Example 1.

The cell suspension was stirred (magnetic stirrer) in a glass vessel at 25° C. and irradiated for 5 minutes by means of three 60W tungsten lamps at a distance of 25 cm. 75 g DFBN was added, and the mixture was kept at 25° C., under irradiation, for 16 hours, at which stage analysis (gc) showed 98.9% conversion of DFBN to DFBAM.

DFBAM crystallised out of solution as it was formed. This crystalline precipitate was recovered directly and recrystallised from ethyl acetate to yield 50.3g DFBAM. After cooling and evaporation of the reaction mixture, a further 16g DFBAM was isolated.

EXAMPLE 3

50μl of a suspension of cells of Rhodococcus Sp. NCIB 12218 in phosphate buffer, was prepared and irradiated as in Example 2, and then added to a solution of 5 μl of DFBN in 1 ml n-heptane. Irradiation and stirring were continued at room temperature. Crystals were deposited. After 1½ hours, a further 10μl of DFBN were added. After 18 hrs, the crystals were filtered off. Analysis showed virtually complete conversion of DFBN to DFBAM.

EXAMPLE 4

A suspension of cells of Rhodococcus Sp. NCIB 12218 in phosphate buffer was prepared as in Examples 1 and 2. 3.2 ml of this suspension was stirred (magnetic stirrer) in a glass vessel at 25° C. and irradiated for 5 minutes as described in Example 2. n-Heptane was added to give a volume of 50ml. Irradiation and stirring continued at a temperature of 28° C., and 3.24g of DFBN was added. GLC analysis showed that 92% of the DFBN was converted to DFBAM after 5 hours.

We claim:

1. A process for the preparation of 2,6-difluorobenzamide which comprises subjecting 2,6-difluorobenzonitrile to the action of *Rhodococcus* sp. NCIB 12218 or a mutant thereof capable of the hydrolysis of 2,6-difluorobenzonitrile to 2,6-difluorobenzamide, under irradiation of light, to form 2,6-difluorobenzamide and recovering the formed 2,6-difluorobenzamide.

2. A biologically pure culture of *Rhodococcus* Sp. NCIB 12218.